United States Patent
Omotowa

(10) Patent No.: US 7,649,121 B2
(45) Date of Patent: *Jan. 19, 2010

(54) PROCESSES FOR PRODUCING HALOGENATED HYDROCARBON COMPOUNDS USING INORGANIC FLUORIDE

(75) Inventor: Bamidele Omotowa, Idaho Falls, ID (US)

(73) Assignee: International Isotopes Inc., Idaho Falls, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 11/853,572

(22) Filed: Sep. 11, 2007

(65) Prior Publication Data

US 2008/0262277 A1    Oct. 23, 2008

Related U.S. Application Data

(60) Provisional application No. 60/912,571, filed on Apr. 18, 2007.

(51) Int. Cl.
*C07C 19/08* (2006.01)

(52) U.S. Cl. ..................................... 570/170
(58) Field of Classification Search .................. None
See application file for complete search history.

(56) References Cited

U.S. PATENT DOCUMENTS

| | | | |
|---|---|---|---|
| 4,070,439 A | 1/1978 | Osaka et al. | |
| 4,876,406 A | 10/1989 | Foulletier et al. | |
| 5,091,602 A * | 2/1992 | Park et al. | 570/167 |
| 5,399,549 A | 3/1995 | Felix et al. | |
| 5,399,796 A | 3/1995 | Correia et al. | |
| 5,446,216 A | 8/1995 | Rao | |
| 5,545,770 A | 8/1996 | Rao | |
| 5,831,136 A | 11/1998 | Rao | |
| 5,841,006 A | 11/1998 | Cuzzato et al. | |
| 5,918,106 A | 6/1999 | Bulko et al. | |
| 6,074,985 A | 6/2000 | Elsheikh et al. | |
| 6,127,586 A | 10/2000 | Scott et al. | |
| 6,229,058 B1 | 5/2001 | Sievert et al. | |
| 6,232,514 B1 | 5/2001 | Cuzzato et al. | |
| 6,268,541 B1 | 7/2001 | Kono et al. | |
| 6,392,106 B1 | 5/2002 | Kono et al. | |
| 6,433,233 B1 | 8/2002 | Kanemura et al. | |
| 6,479,718 B1 | 11/2002 | Elsheikh et al. | |
| 6,503,865 B1 | 1/2003 | Kanemura et al. | |
| 6,841,705 B2 | 1/2005 | Yuichi et al. | |
| 7,067,707 B2 | 6/2006 | Piepho et al. | |
| 7,071,368 B1 | 7/2006 | Merkel et al. | |
| 7,074,973 B2 | 7/2006 | Nappa et al. | |
| 2001/0049457 A1 * | 12/2001 | Stephens | 570/123 |
| 2008/0262274 A1 | 10/2008 | Omotowa | |
| 2008/0262275 A1 | 10/2008 | Omotowa | |
| 2008/0262276 A1 | 10/2008 | Omotowa | |

OTHER PUBLICATIONS

Park et al., Kongop Hwahak (1993), 4(2), 318-23.*
Okazaki et al., Kogyo Kagaku Zasshi (1969), 72(3), 630-3.
Schumb, W.C., "Some Metathetical Reactions of the Gaseous Fluorides of Group IV," Journal of the American Chemical Society, vol. 74, Jun. 1951, pp. 1754-1760.

(Continued)

Primary Examiner—Karl J Puttlitz
(74) Attorney, Agent, or Firm—Perkins Coie LLP

(57) ABSTRACT

Methods and systems for producing halogenated hydrocarbon compounds with an inorganic fluoride (e.g., germanium tetrafluoride ($GeF_4$)) are disclosed herein.

26 Claims, 6 Drawing Sheets

OTHER PUBLICATIONS

U.S. NonFinal Office Action dated Apr. 11, 2008 under U.S. Appl. No. 11/853,521, 8 pages.

U.S. NonFinal Office Action dated Mar. 14, 2008 under U.S. Appl. No. 11/853,541, 8 pages.

U.S. NonFinal Office Action dated Mar. 14, 2008 under U.S. Appl. No. 11/853,557, 8 pages.

U.S. Appl. No. 12/203,654, filed Sep. 3, 2008, Omotowa.

Christe et al. Silicon Tetrafluoride, a New Fluorinating Agent, 1964, J. Org. Chem., p. 3007-3009.

International Search Report and Written Opinion; International Application No. PCT/US08/75133; Filed Sep. 3, 2008; Applicant: International Isotopes Inc.; Mailed Nov. 24, 2008, 10 pages.

International Search Report and Written Opinion; International Application No. PCT/US08/59929; Filed Apr. 10, 2008; Applicant: International Isotopes Inc.; Mailed Sep. 29, 2008, 10 pages.

International Search Report and Written Opinion; International Application No. PCT/US08/59933; Filed Apr. 10, 2008; Applicant: International Isotopes Inc.; Mailed Aug. 25, 2008, 10 pages.

International Search Report and Written Opinion; International Application No. PCT/US08/59942; Filed Apr. 10, 2008; Applicant: International Isotopes Inc.; Mailed Sep. 12, 2008, 9 pages.

International Search Report and Written Opinion; International Application No. PCT/US08159937; Filed Apr. 10, 2008; Applicant: International Isotopes Inc.; Mailed Aug. 25, 2008, 9 pages.

* cited by examiner

US 7,649,121 B2

PROCESSES FOR PRODUCING HALOGENATED HYDROCARBON COMPOUNDS USING INORGANIC FLUORIDE

CROSS-REFERENCE TO RELATED APPLICATION

This application claims priority to Provisional U.S. Patent Application No. 60/912,571, entitled "Processes for Production of Hydrofluorocarbon Using Inorganic Fluoride From Pentachloroethane," filed Apr. 18, 2007, the disclosure of which is incorporated herein by reference in its entirety. This application is also related to U.S. patent application, Ser. No. 11/853,521, entitled "Processes for Producing Hydrofluorocarbon Compounds Using Inorganic Fluoride", U.S. patent application, Ser. No. 11/853,541, entitled "Processes for Producing Chlorofluorocarbon Compounds Using Inorganic Fluoride", and U.S. patent application, Ser. No. 11/853,557, entitled "Processes for Producing Halocarbon Compounds Using Inorganic Fluoride", the disclosures of which are incorporated herein by reference in their entirety.

TECHNICAL FIELD

The present disclosure is related to processes for producing halogenated hydrocarbon compounds (e.g., hydrochlorofluorocarbon compounds). In particular, the present disclosure is related to processes for producing 1,2-substituted haloalkanes, such as 1,1,2,2-pentachloro-2-fluoroethane (HCFC-121) and/or 1,1,2-trichloro-2,2-difluoroethane (HCFC-122).

BACKGROUND

Chlorofluorocarbon (CFC) and hydrochlorofluorocarbon (HCFC) compounds have been used as refrigerants, fire extinguishing agents, propellants, and solvents since the early twentieth century. However, CFC and HCFC compounds are now believed to deplete the ozone layer of the earth via UV-promoted reactions. As a result, the U.S. Environmental Protection Agency has already banned the production and importation of certain products comprising CFC and HCFC compounds.

Internationally, the Montreal Protocol has set out plans for replacing CFC and HCFC compounds with hydrofluorocarbon (HFC) compounds. However, the cost of producing HFC compounds is considerably higher than that of producing CFC or HCFC compounds. Presently, industrial fluorination processes for producing HFC are based on hydrogen fluoride (HF) fluorination of chlorocarbons. FIG. 1 presents examples of known potential multistep routes to produce, e.g., HFC-125 and HFC-134a.

As illustrated in FIG. 1, multistep processes are typically required to produce desired hydrofluorocarbon compounds. For example, HFC-125 can be produced by first converting either triclene or perclene into 1,1-dichloro-2,2,2-trifluoroethane (HCFC-123) and then fluorinating HCFC-123 to 2-chloro-1,1,1,2-tetrafluoroethane (HCFC-124). HFC-125 can then be produced by performing chlorine-fluorine exchange on HCFC-124 with hydrogen fluoride. Similarly, as illustrated in FIG. 1, HFC-134a can also be produced with either triclene or perclene using multistep processes.

The processes for producing HFC-125 and HFC-134a are more complex, both chemically and operationally, than those for CFC and HCFC compounds. Moreover, both the triclene and perclene processes require disposing of hydrogen chloride (HCl) byproducts. Procedures and equipment are available to convert some of the HCl byproducts into a chlorine ($Cl_2$) gas and subsequently recycle the chlorine gas back into the production process. Nonetheless, this recycling operation adds to the cost of the overall HFC production process. Therefore, there is a need to develop more efficient and cost-effective processes for producing halogenated hydrocarbon compounds.

DETAILED DESCRIPTION

Figure 1:
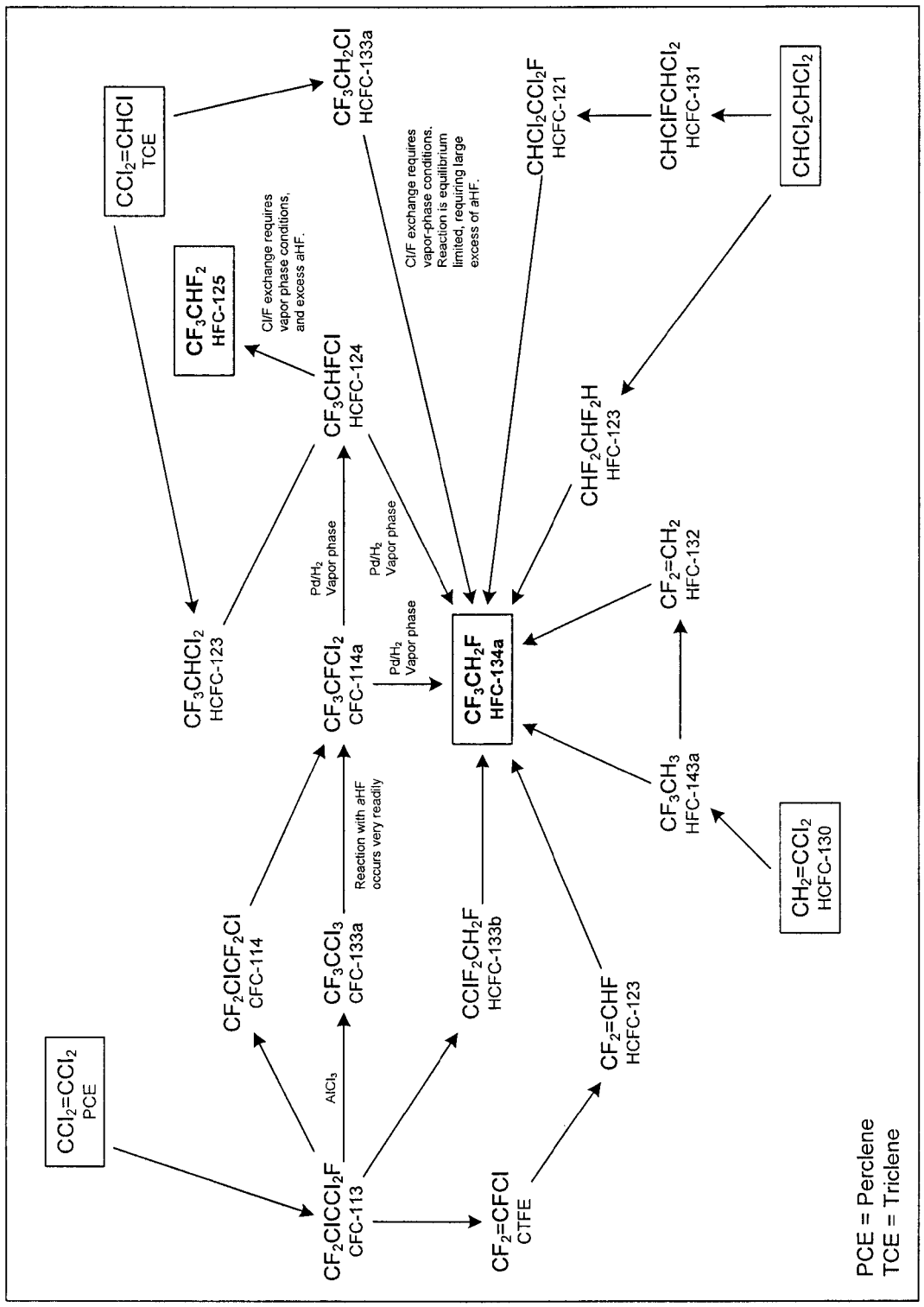
FIG. 1 is a schematic diagram illustrating potential routes to HFC-125 and HFC-134a in accordance with the prior art.

Specific details of several embodiments of the disclosure are described below with reference to processes for efficiently and cost-effectively producing halogenated hydrocarbon compounds from halogenated carbon compounds. The term "halogenated hydrocarbon compounds" generally refers to halogen-substituted (e.g., fluorine-, chlorine-, bromine-, and/or iodine-substituted) organic compounds containing carbon and hydrogen. Examples of halogenated hydrocarbon compounds include hydrofluorocarbon compounds containing fluorine, carbon, and hydrogen, hydrochlorocarbon compounds containing chlorine, carbon, and hydrogen, and hydrochlorofluorocarbon compounds containing fluorine, chlorine, carbon, and hydrogen. The term "halogenated carbon compounds" generally refers to halogen-substituted organic compounds containing only carbon and halogen. Examples of halogenated carbon compounds include fluorocarbon compounds containing fluorine and carbon and chlorocarbon compounds containing chlorine and carbon. Several other embodiments of the invention may have different configurations, components, or procedures than those described in this section. A person of ordinary skill in the art, therefore, will accordingly understand that the invention may have other embodiments with additional elements, or the invention may have other embodiments without several of the elements shown and described below.

One aspect of the present disclosure is directed to the use of an inorganic fluoride as a fluorinating agent for producing hydrochlorofluorocarbon (HCFC) compounds, e.g., HCFC-121 and HCFC-122. The following description uses germanium tetrafluoride ($GeF_4$) as an example of an inorganic fluoride to show various embodiments of the fluorination reaction of the present disclosure for illustration purposes. However, a skilled artisan will appreciate that $GeF_4$ is merely an example of an inorganic fluoride. Other inorganic fluorides for use in the systems and processes can include at least one of bromine trifluoride ($BrF_3$), manganese tetrafluoride ($MnF_4$), sulfur tetrafluoride ($SF_4$), bromine pentafluoride ($BrF_5$), and tungsten hexafluoride ($WF_6$).

Another aspect of the present disclosure relates to producing HCFC-121 and HCFC-122 in the fewest number of reaction steps by employing appropriate starting material. In one embodiment, the present disclosure relates to producing HCFC-121 and HCFC-122 from 1,1,2,2,2-pentachloroethane (referred to as pentachloroethane hereinafter) in one reaction step. The inventor has observed that the reaction described above has an unexpectedly high yield (about 60-76%) and a good selectivity, e.g., about 3.0, toward HCFC-122 in certain embodiments.

A further aspect of the present disclosure is directed to using one or more catalysts to catalyze a fluorination reaction using an inorganic fluoride via halogen exchange in the presence of a chlorocarbon compound. It is believed that, in certain embodiments, the class of compounds known as superacids and/or Lewis acids can catalyze such fluorination reaction. The term "superacid" generally refers to an acid with an acidity greater than that of 100% sulfuric acid ($H_2SO_4$). Examples of superacids include trifluoromethane sulfonic acid ($CF_3SO_3H$) and fluorosulfuric acid ($FSO_3H$). The term "Lewis acid" generally refers to a compound that is an electrophile or an electron acceptor. Examples of Lewis acids include aluminum trichloride ($AlCl_3$), iron trichloride ($FeCl_3$), boron trifluoride ($BCl_3$), niobium pentachloride ($NbCl_5$), and the lanthanide triflates, e.g., ytterbium(III) triflate. In certain embodiments, aluminum trichloride ($AlCl_3$) can be used to react with $GeF_4$ to form $AlCl_xF_y$ (x+y=3), in situ, which has been observed to catalyze the $GeF_4$ fluorination of chlorocarbons. In other embodiments, an antimony halide (e.g., antimony pentachloride ($SbCl_5$)), can be used to react with $GeF_4$ to form $SbCl_xF_y$ species (where x+y=5), in situ. In other embodiments, $SbCl_3$, $SbF_5$, $SbF_3$, $AsF_5$, $AsCl_3$, $TaCl_5$, $TaF_5$, $NbCl_5$, $NbF_5$, $HSO_3F$, $CF_3SO_3F$, $Cr_2O_3$, and/or other suitable superacids and/or Lewis acids can also be used to catalyze a fluorination of chlorocarbons in the presence of, e.g., $GeF_4$.

Reaction Systems

Figure 2:
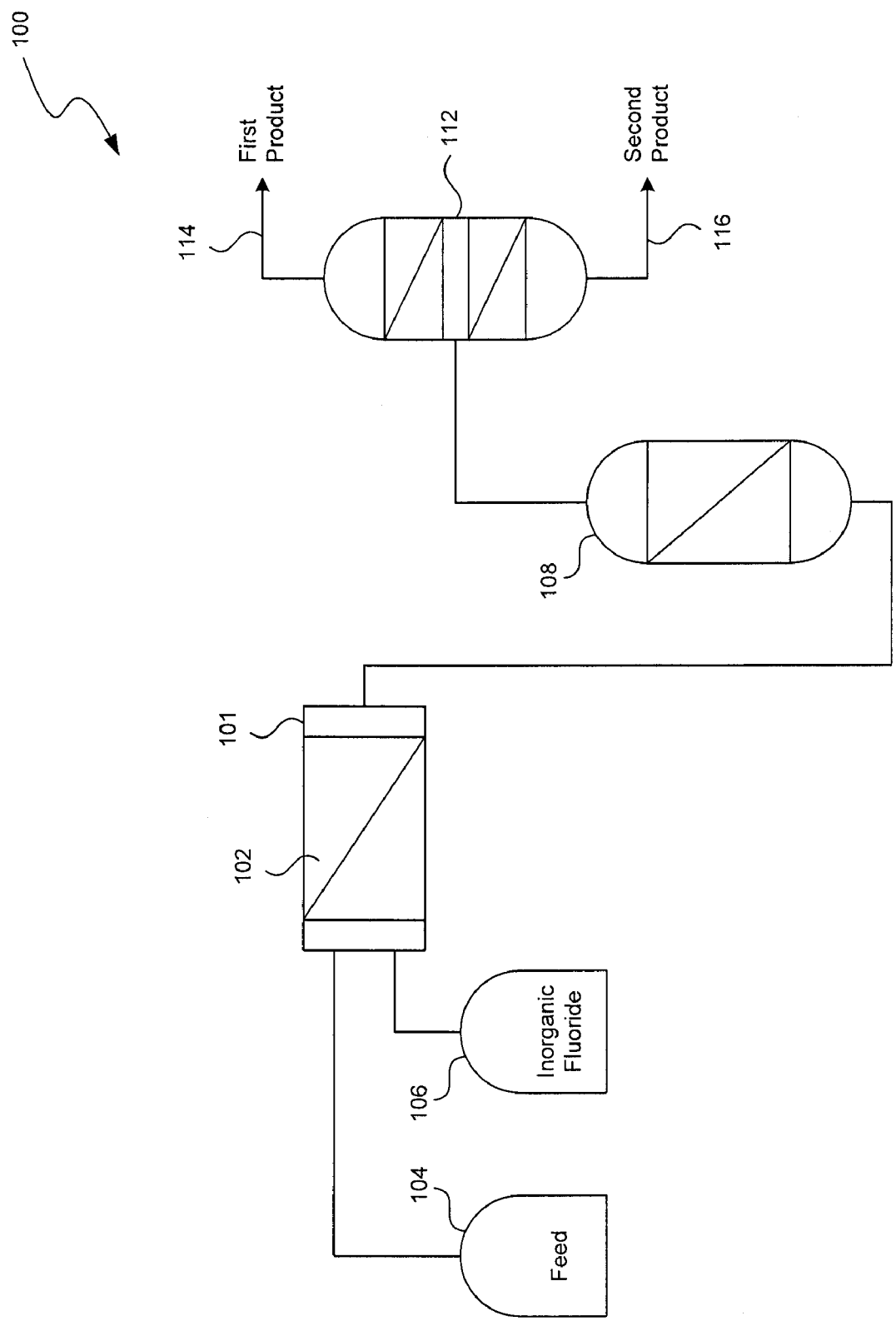
FIG. 2 is a schematic diagram illustrating a system for producing halogenated hydrocarbon compounds in accordance with an embodiment of the disclosure.

FIG. 2 is a schematic diagram illustrating a system 100 for producing halogenated hydrocarbon compounds in accordance with an embodiment of the disclosure. The system 100 can include a reactor 101 operatively coupled to a feed storage 104 containing an organic reactant (e.g., an organic compound such as pentachloroethane), and an inorganic fluoride storage 106 containing, e.g., $GeF_4$. The reactor 101 can be configured generally as a tubular reactor constructed from Inconel, Hastelloy, and/or other fluorine-resistant material. In some embodiments, the reactor 101 can include a catalyst bed 102 containing $AlCl_3$, $SbCl_5$, and/or other suitable catalyst. In other embodiments, the catalyst bed 102 can be omitted from the reactor 101, and a catalyst (e.g., $AlCl_3$ and/or $SbCl_5$) can be fed into the reactor 101 during operation.

The system 100 can include a scrubber 108 that receives a reaction product from the reactor 101. The scrubber 108 can be configured to remove impurities and/or unreacted material from the product. For example, in one embodiment, the scrubber 108 includes a liquid base containing, e.g., potassium hydroxide (KOH), sodium hydroxide (NaOH), and/or other base, for absorbing, reacting, and/or otherwise combining with unreacted inorganic halide (e.g., $GeF_4$). In another embodiment, the scrubber 108 includes a solid base (e.g., pellets) containing KOH, NaOH, and/or other base. In further embodiments, the scrubber 108 can include both a liquid base and a solid base for removing unreacted halide.

The system 100 can further include a separator 112 downstream of the scrubber 108. The separator 112 can be configured to split halogenated hydrocarbon compounds in the reaction product. In the illustrated embodiment, the separator 112 includes a distillation column that can produce a first product from a top end 114 and a second product from a bottom end 116. For example, the first product can include HCFC-121, and the second product can include HCFC-122. In other embodiments, the separator 112 can also include a flash tank, a cyclone, and/or other liquid-liquid separation/liquid-gas separation devices. In further embodiments, instead of producing the first and second products from the top end 114 and the bottom end 116, the separator 112 can also produce products from locations intermediate the top end 114 and the bottom end 116 based on the volatility profile of the reaction product.

In operation, the reactor 101 first receives a feed stream (also referred to as a reaction feed) containing, for example, pentachloroethane from the feed storage 104 and an inorganic fluoride (e.g., $GeF_4$) from the inorganic fluoride storage 106. In one embodiment, $GeF_4$ can be in the stoichiometric amount required to fluorinate pentachloroethane in the reaction feed. For example, the molar ratio of $GeF_4$ to pentachloroethane can be about 1.12:1. In other embodiments, $GeF_4$ can be in molar excess of the stoichiometric amount required. For example, the molar ratio of $GeF_4$ to pentachloroethane in the reaction feed can be about 3:1. In further embodiments, the organic reactant can be in molar excess. For example, the molar ratio of $GeF_4$ to pentachloroethane in the reaction feed can be about 0.6.

In the reactor 101, $GeF_4$ and pentachloroethane in the reaction feed contact the catalyst (e.g., $AlCl_3$ and/or $SbCl_5$) held in the catalyst bed 102. The reactor 101 can be at a temperature of about 60° to about 90° C. and at a pressure of about 50 to 80 psig. Under such temperature and pressure conditions, the inventor has observed that pentachloroethane can react with $GeF_4$ in the reaction feed to form HCFC-121 and HCFC-122 in a liquid phase reaction. Other potential fluorination products such as 1,2,2,2-tetrachloro-1-fluoroethane ($CHClFCCl_3$), 1,1,1-trichloro-2,2-difluoroethane ($CHF_2CCl_3$), 1,1-dichloro-2,2,2-trifluoroethane ($CHCl_2CF_3$), 1,2-dichloro-1,2,2-trifluoroethane ($CHClFC-ClF_2$), 1-chloro-1,2,2,2-tetrafluoroethane ($CHClFCF_3$), 1-chloro-1,1,2,2-tetrafluoroethane ($CHF_2CClF_2$), or other hydrohalocarbon compounds were not observed.

There have been prior unsuccessful attempts to use $GeF_4$ for fluorination of chlorocarbons such as pentachloroethane. The inventor has recognized that those prior experiments failed, at least in part, because of the omission of an appropriate catalyst. The inventor has also recognized that $SbCl_5$, $AlCl_3$, and/or other Lewis acid catalysts can cause $GeF_4$ to readily react with pentachloroethane in a liquid phase reaction. Without being bound by theory, it is believed that $GeF_4$ can first react with the catalyst (e.g., $SbCl_5$) to form a series of equilibria between $SbCl_5$ and $GeF_4$ as follows:

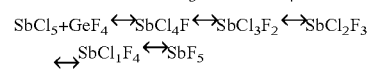

It is believed that the $SbCl_xF_y$ (x+y=5) compounds may then act as Lewis acid catalysts to lower the activation energy for fluorinating pentachloroethane. It is also believed that $SbF_5$ is a more efficient catalyst than $SbCl_4F$, $SbCl_3F_2$, $SbCl_2F_3$, and $SbClF_4$. Thus, in some embodiments, the reaction equilibria can be shifted toward $SbF_5$ by, for example, adding excess $GeF_4$ to the reaction feed, removing products from the reaction, and/or using other suitable techniques.

In one embodiment, the reaction described above can be carried out in a batch mode. For example, the reaction conditions can be maintained in the reactor 101 until the reaction is completed, and then the reaction product can be discharged from the reactor 101 to the scrubber 108. In other embodiments, the reaction described above can be carried out in a continuous mode. For example, the reactor 101 can be configured as a plug-flow reactor, a constantly stirred tank reactor, and/or other types of reactor with sufficient residence time to allow the completion of the reaction in a continuous operation.

After the reaction is completed, in one embodiment, the reaction product can be separated into a gas phase product and a liquid phase product by, e.g., decanting the reaction product. The liquid phase product then flows from the reactor 101 to the scrubber 108 for removing impurities and/or unreacted material from the product. For example, if $GeF_4$ is in molar excess of pentachloroethane in the reaction feed, some $GeF_4$ is likely to remain in the liquid phase product after the reaction is completed. In one embodiment, the scrubber 108 can contain KOH and/or NaOH that reacts with the excess $GeF_4$ in order to purify the liquid phase product. In other embodiments, the scrubber 108 can remove the excess $GeF_4$ and/or other byproducts using other physical and/or chemical techniques.

In one embodiment, the separator 112 then splits the liquid phase product to produce the first product containing essentially HCFC-121 from the top end 114 and the second product containing essentially HCFC-122 from the bottom end 116. At one atmospheric pressure, HCFC-121 has a boiling point of 73° C., and HCFC-122 has a boiling point of 116° C. As a result, the relative volatility between HCFC-121 and HCFC-122 is sufficient to enable ready separation between these two compounds.

Fluorination reaction carried out in the system 100 described above can efficiently and cost-effectively produce HCFC-121, HCFC-122, and/or other hydrofluorocarbon compounds. Unlike conventional techniques having multiple reaction steps, using the system 100 can produce these compounds in one reaction step via direct chlorine-fluorine exchange on pentachloroethane. The reaction has been observed to produce an unexpectedly high yield of pentachloroethane conversion of at least about 60%, more preferably at least about 63%, and even more preferably at least about 76%. The reaction has also been observed to produce a good selectivity of at least about 1:1, more preferably about 2.1, and even more preferably about 3.0 toward HCFC-122 by controlling the molar ratio between pentachloroethane and $GeF_4$. For example, a molar ratio of about 3:1 ($GeF_4$ to pentachloroethane) is believed to result in a reaction product containing about 98% HCFC-122. A molar ratio of about 0.6:1 ($GeF_4$ to pentachloroethane) is believed to result in a reaction product containing about 74% HCFC-122 and 26% HCFC-121. Moreover, the reaction, in one embodiment, has been observed to produce only HCFC-121 and HCFC-122, which have sufficiently different volatility to enable ready separation of the reaction product.

Even though the system 100 described above has a one-pass configuration, in certain embodiments, the system 100 can also have at least one recycle loop. For example, in some embodiments, unreacted reaction feed and/or other compounds can be recycled back to the reactor 101. Moreover, the system 100 can have other process configurations with additional and/or different processing devices. For example, in some embodiments, the system 100 can include a stand-alone decanter for removing the gas phase product from the liquid phase product. In other embodiments, the catalyst can be mixed with the reaction feed and/or supplied to the reactor 101 during operation.

Method for Producing Halogenated Hydrocarbon Compounds

Figure 3:
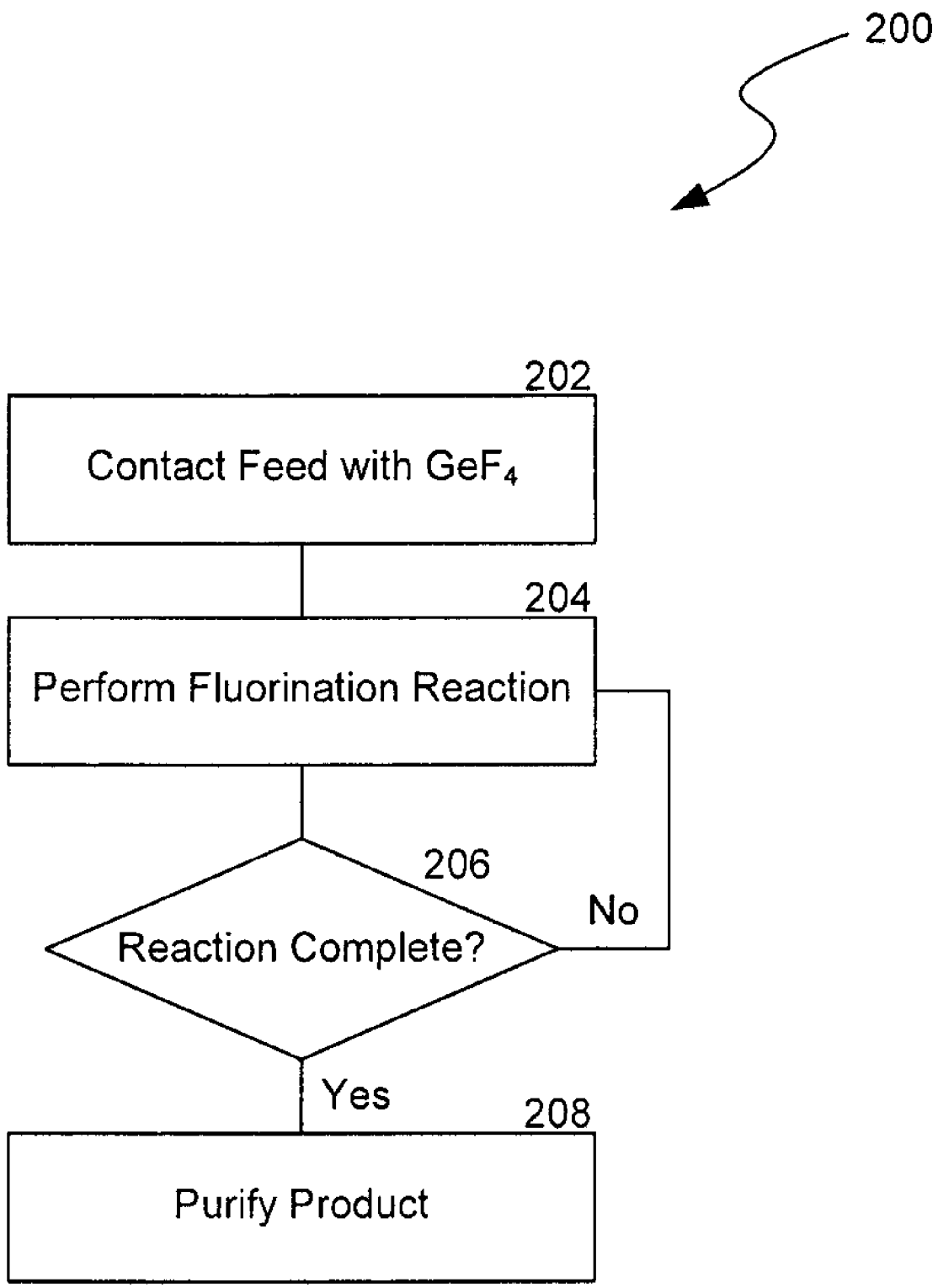
FIG. 3 is a flow chart illustrating a method for producing halogenated hydrocarbon compounds in accordance with an embodiment of the disclosure.

FIG. 3 is a flow chart illustrating a method 200 for producing halogenated hydrocarbon compounds in accordance with an embodiment of the disclosure. The method 200 can include contacting a reaction feed containing a chlorocarbon compound (e.g., pentachloroethane) with a fluorinating agent (e.g., $GeF_4$) in the presence of a metal halide catalyst at block 202. In one embodiment, the metal halide catalyst includes $SbCl_5$, and a molar ratio of $SbCl_5$/pentachloroethane/$GeF_4$ can be about 1:A:B (2<A<10 and 2<B<8). In other embodiments, the metal halide catalyst can include $AlCl_3$, $SbF_3$, $AsF_5$, $AsCl_3$, $TaCl_5$, $TaF_5$, $NbCl_5$, $NbF_5$, $HSO_3F$, $CF_3SO_3F$, $Cr_2O_3$, and/or other suitable inorganic halide compounds. The method 200 then includes performing a fluorination reaction (e.g., by chlorine-fluorine exchange) on pentachloroethane in the reaction feed at block 204 as follows:

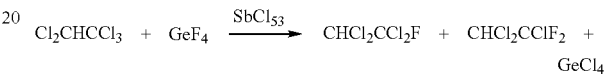

Suitable reaction temperatures can be about 60° to about 90° C., and suitable pressures can be about 50 to 80 psig. Under such temperature and pressure conditions, the reaction is believed to be generally a liquid phase reaction.

A decision is made at block 206 to determine whether the reaction is complete. In one embodiment, the decision can be based on a reaction time (e.g., 6-8 hours). In another embodiment, the decision can be based on a conversion of the reaction and/or other reaction parameters. For example, an operator can periodically sample the material in the reactor 101 to determine a concentration of pentachloroethane. If the concentration of pentachloroethane is below a threshold, then the reaction is indicated to be completed.

If the reaction is completed, the method 200 further includes purifying the reaction product at block 208. Purifying the reaction product can include separating a liquid phase product from a gas phase product, removing byproducts and/or other impurities from the liquid phase product, and splitting halogenated hydrocarbon compounds in the liquid phase product using condensation, distillation, liquid-liquid extraction, liquid-gas separation, and/or other suitable techniques. If the reaction is not completed, the process reverts to performing the chlorine-fluorine exchange on pentachloroethane at block 204.

EXAMPLES

Figure 4:
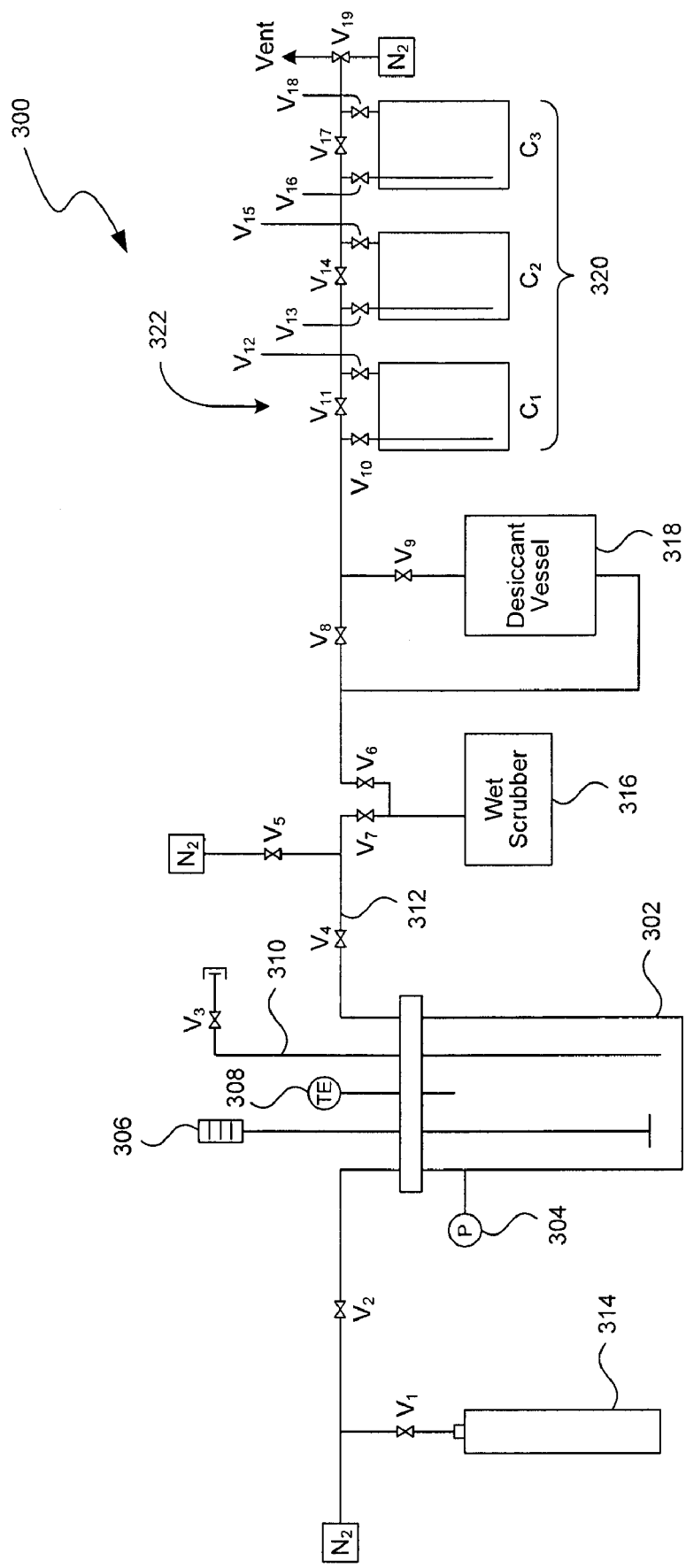
FIG. 4 is a schematic diagram illustrating a system for producing halogenated hydrocarbon compounds in accordance with an embodiment of the disclosure.

Experiments were conducted to fluorinate pentachloroethane using $GeF_4$ in the presence of $SbCl_5$ in a bench-top reactor (Model No. 4563) supplied by the Parr Instrument Company of Moline, Ill. FIG. 4 is a schematic diagram illustrating an experimental system 300 for producing halogenated hydrocarbon compounds in accordance with an embodiment of the disclosure.

As shown in FIG. 4, the system 300 includes an Inconel 600 reactor 302 having a volume of about 600 mL. The reactor 302 includes a pressure monitor 304, a mixer 306, and a temperature monitor 308. The reactor 302 also includes a liquid sample line 310 and a gas sample line 312. The system 300 also includes a cylinder 314 holding gaseous $GeF_4$ (187 psig at 21° C.). The system 300 also includes a 200 mL wet scrubber 316 containing KOH and a desiccant vessel 318 containing Al$_2$O$_3$ and KOH pellets. The system 300 further includes three 75 mL sampling cylinders 320 (labeled C$_1$-C$_3$). The sampling cylinders 320 can be held at various temperatures and pressures for collecting materials with different boiling points. Various components of the system 300 can be isolated using a plurality of valves 322 (labeled V$_1$-V$_{19}$).

All chemicals used in the following experiments were obtained commercially from Aldrich-Sigma, Inc. of Milwaukee, Wis. The GeF$_4$ gas was produced by International Isotopes, Inc. of Idaho Falls, Id. Fourier transform infrared (FTIR) spectra were recorded on a MIDAC I1201 bench-top infrared spectrometer as neat liquids between potassium bromide (KBr) plates or gas samples in a 10 cm path-length demountable gas cell with zinc-selenium (ZnSe) windows. 1H, 13C, and $^{19}$F NMR spectra were obtained on a 300 MHz Bruker AMX spectrometer at 200, 50, and 188 MHz, respectively, by using CDCl$_3$ as a locking solvent. Chemical shifts were reported relative to Me$_4$Si or CFCl$_3$. GC-MS spectra were obtained with a Shimadzu Q5050 spectrometer (EI-mode). Elemental analyses were performed by the Desert Analytics Laboratory of Tucson, Ariz.

Experiment I

Pentachloroethane (46.7 g, 0.232 mol) and fuming antimony pentachloride (6.6 g, 0.022 mol) were combined in a 40 mL high density polyethylene (HDPE) plastic container. The mixture was poured into the reactor 302 in a nitrogen atmosphere. The reactor was closed and bolted. Germanium tetrafluoride (19.45 g, 0.131 mol) was supplied to the reactor 302 at 21° C. in a vented hood, and the pressure in the reactor 302 was 67 psig. The gas-in and gas-out valves on the reactor 302 were closed to isolate the reagents in the reactor 302 while the supply sample line was purged several times and then disconnected. The reactor 302 was then transferred into a heating mantle and connected to the wet scrubber 316, the desiccant vessel 318, and the sampling cylinders 320. The heating mantle warmed the reactor 302 and its contents to about 60° C. When the reactor 302 was warmed to about 40° C., the pressure in the reactor 302 dropped to about 38 psig. After eight hours, heating was discontinued, and the reactor 302 was allowed to cool to the room temperature. The pressure in the reactor 302 was 6 psig at 19° C. The gas phase product was vented through the gas-out valve to the wet scrubber 316 until the pressure of the reactor 302 dropped to about zero psig. Germanium halide byproducts were recovered as insoluble germanium (IV) oxide. Subsequently, the reactor 302 was pressurized several times with nitrogen to about 90 psig and vented through the scrubber 316. The reactor 302 was then opened in the vented hood. A fuming liquid product was poured from the reactor 302 into a 50 mL HDPE plastic container. About 5 g of dark brown solid residue was observed around the bottom of the reactor 302. The liquid product was poured into 60 mL of deionized water. A liquid phase product was then obtained and dried with MgSO$_4$ in a 100 mL glass flask. The liquid phase product was fractionated to obtain a first fraction of about 6.8 g of HCFC-121 and a second fraction of about 18.8 g of HCFC-122. The combined yield was about 76%.

Experiment II

Another experiment was carried out following a procedure similar to that of Experiment I with a different molar ratio of the reagents. In particular, the reactor 302 was charged with about 24.2 g (0.103 mol) pentachloroethane, about 2.0 g (0.007 mol) of SbCl$_5$, and about 46.7 g (0.314 mol) of GeF$_4$. The pressure in the reactor 302 was 190 psig when GeF$_4$ was introduced. The pressure rose to about 256 psig at 90° C. and dropped to about 40 psig when cooled to 21° C. Analysis by FTIR, NMR, and GC-MS showed that selectivity of the reaction product was greater than about 98% toward HCFC-122. The reaction produced about 12.7 g of HCFC-122 with a yield of about 63%. HCFC-123 was not observed in the reaction product.

Experimental Results

Pentachloroethane reacted readily with GeF$_4$ in the liquid phase in the presence of a superacid and/or a Lewis acid catalyst such as SbCl$_5$. As shown in the FTIR analysis results in FIGS. 5 and 6, the reaction produced only HCFC-121 and HCFC-122 in both Experiments I and II while other potential fluorinating products were not observed. The results from cryogenic distillation and FTIR analysis of the reaction product and selected reaction conditions of Experiments I and II described above are listed in the table below:

| | | | | Product Selectivity | |
|---|---|---|---|---|---|
| Reaction | Molar Ratio (SbCl$_5$/C—Cl/GeF$_4$) | Yield | Condition (P/T/Time) | HCFC-121 | HCFC-122 |
| Exp. I | 1:10:6 | 76% | 70 psig/ 60° C./8 hr | 26% | 74% |
| Exp. II | 1:15:45 | 63% | 256 psig/ 90° C./8 hr | | 98% |

Figure 5:
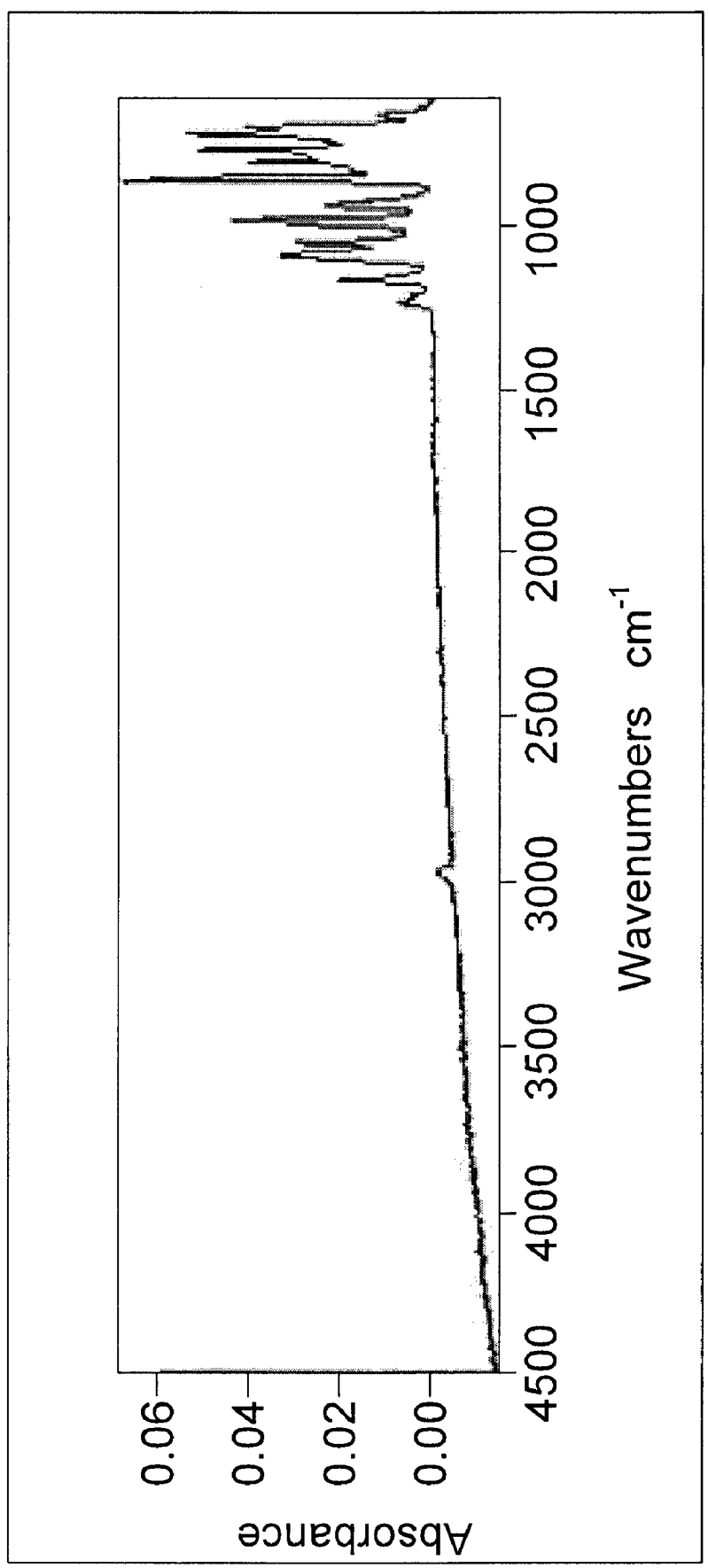
FIG. 5 is a Fourier transform infrared (FTIR) scan of a reaction product prepared in accordance with an embodiment of the disclosure.
Figure 6:
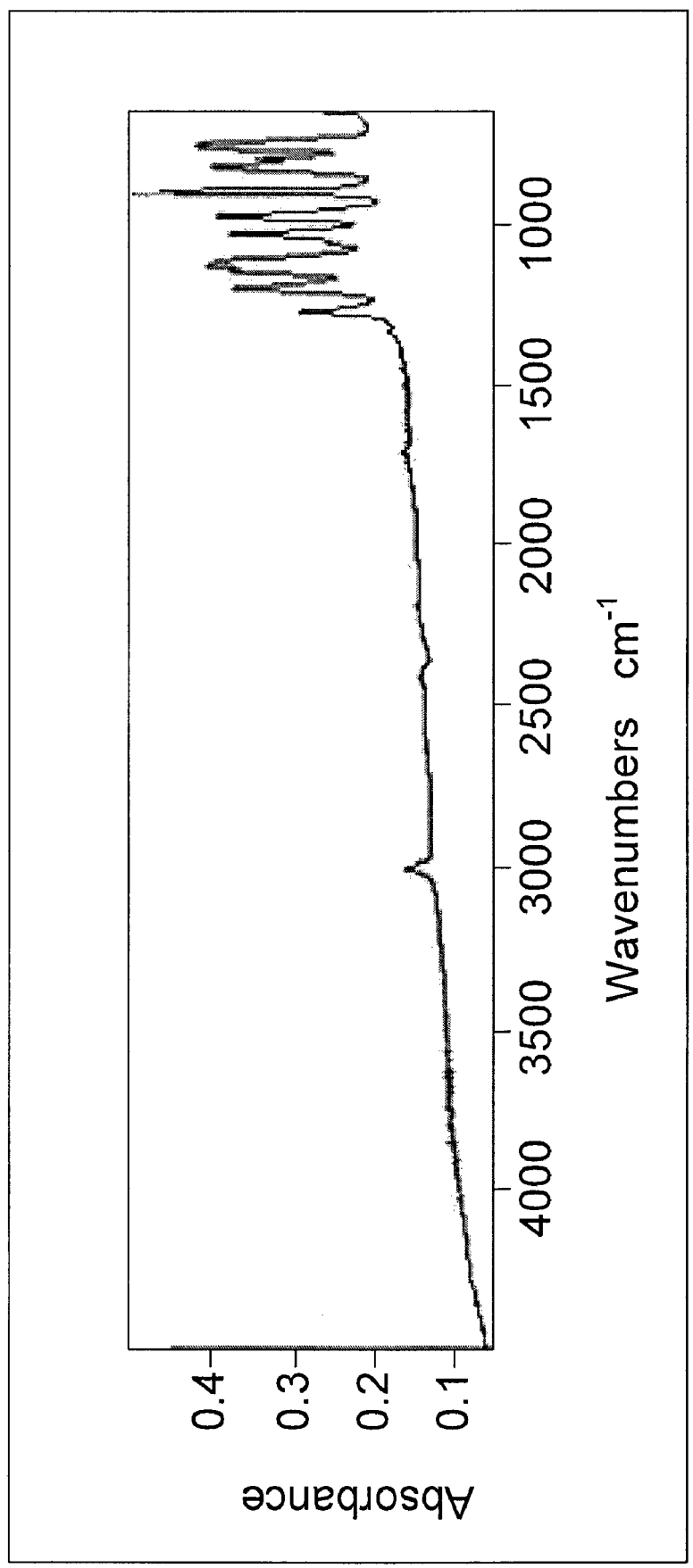
FIG. 6 is a Fourier transform infrared (FTIR) scan of another reaction product prepared in accordance with another embodiment of the disclosure.

As can be seen from the table above and FIGS. 5 and 6, both Experiments I and II produced HCFC-121 and/or HCFC-122 with high yield (i.e., ≧about 63%, or ≧about 76%) and a good selectivity (i.e., at least about 74% and up to about 98%) toward HCFC-122 from inexpensive starting material such as pentachloroethane.

From the foregoing, it will be appreciated that specific embodiments of the invention have been described herein for purposes of illustration, but that various modifications may be made without deviating from the invention. Elements of one embodiment may be combined with other embodiments in addition to or in lieu of the elements of the other embodiments. Accordingly, the invention is not limited except as by the appended claims.

I claim:

1. A method for producing a halogenated hydrocarbon compound, comprising reacting a chlorocarbon compound and/or a chlorofluorocarbon compound with germanium tetrafluoride (GeF$_4$) in the presence of a catalyst containing an antimony (Sb) halide.

2. The method of claim 1 wherein reacting a chlorocarbon compound and/or a chlorofluorocarbon compound with germanium tetrafluoride (GeF$_4$) includes reacting 1,1,2,2,2-pentachloroethane with germanium tetrafluoride in the presence of a catalyst containing antimony pentachloride (SbCl$_5$).

3. The method of claim 2 wherein reacting a chlorocarbon compound and/or a chlorofluorocarbon compound with germanium tetrafluoride (GeF$_4$) includes reacting 1,1,2,2,2-pentachloroethane with germanium tetrafluoride in the presence of a catalyst containing antimony pentachloride at a temperature of about 60° to about 90° C.

4. The method of claim 2 wherein reacting a chlorocarbon compound and/or a chlorofluorocarbon compound with germanium tetrafluoride (GeF$_4$) includes reacting 1,1,2,2,2-pentachloroethane with germanium tetrafluoride in the presence of a catalyst containing antimony pentachloride in a liquid phase reaction.

5. The method of claim 2, further comprising reacting germanium tetrafluoride with antimony pentachloride to form at least one of antimony chlorotetrafluoride ($SbClF_4$), antimony dichlorotrifluoride ($SbCl_2F_3$), antimony trichlorodifluoride ($SbCl_3F_2$), and antimony tetrachlorofluoride ($SbCl_4F$).

6. The method of claim 5, further comprising shifting the equilibrium toward antimony trifluoride.

7. The method of claim 2, further comprising maintaining a molar ratio of germanium tetrafluoride to antimony pentachloride of about 0.6 to about 15.

8. The method of claim 2, further comprising maintaining a molar ratio of germanium tetrafluoride to 1,1,2,2,2-pentachloroethane of about 1 to about 4.

9. The method of claim 2 wherein reacting a chlorocarbon compound and/or a chlorofluorocarbon compound with germanium tetrafluoride ($GeF_4$) includes reacting 1,1,2,2,2-pentachloroethane with germanium tetrafluoride in the presence of the catalyst, further comprising producing at least one of 1,1,2,2-pentachloro-2-fluoroethane ($CHCl_2CCl_2F$) and 1,1,2-trichloro-2,2-difluoroethane ($CHCl_2CClF_2$) without producing at least one of 1,2,2,2-tetrachloro-1-fluoroethane ($CHClFCCl_3$), 1,1,1-trichloro-2,2-difluroethane ($CHF_2CCl_3$), 1,1-dichloro-2,2,2-trifluoroethane ($CHCl_2CF_3$), 1,2-dichloro-1,2,2-trifluoroethane ($CHClFCClF_2$), 1-chloro-1,2,2,2-tetrafluoroethane ($CHClFCF_3$), and 1-chloro-1,1,2,2-tetrafluoroethane ($CHF_2CClF_2$).

10. A method for producing hydrofluorocarbon compounds, comprising contacting a reaction feed containing a chlorocarbon compound and/or a chlorofluorocarbon compound and germanium tetrafluoride ($GeF_4$) with a catalyst containing antimony pentachloride ($SbCl_5$) in a reactor, thereby fluorinating the chlorocarbon compound and/or the chlorofluorocarbon compound.

11. The method of claim 10 wherein the reaction feed includes 1,1,2,2,2-pentachloroethane, and the method further includes producing a reaction product containing at least one of 1,1,2,2-pentachloro-2-fluoroethane ($CHCl_2CCl_2F$) and 1,1,2-trichloro-2,2-difluoroethane ($CHCl_2CClF_2$).

12. The method of claim 10 wherein contacting a reaction feed includes contacting the reaction feed with a catalyst bed of the reactor, the catalyst bed holding the catalyst containing antimony pentachloride.

13. The method of claim 10, further comprising performing chlorine-fluoride exchange on the chlorocarbon compound and/or the chlorofluorocarbon compound of the reaction feed in the presence of the catalyst.

14. The method of claim 10 wherein the reaction feed includes 1,1,2,2,2-pentachloroethane, and the method further includes reacting 1,1,2,2,2-pentachloroethane with germanium tetrafluoride at a temperature of about 60° C. to about 90° C.

15. The method of claim 10 wherein the reaction feed includes 1,1,2,2,2-pentachloroethane, and the method further includes reacting 1,1,2,2,2-pentachloroethane with germanium tetrafluoride at a molar ratio of about 1:10:6 for antimony chloride/1,1,2,2,2-pentachloroethane/germanium tetrafluoride.

16. The method of claim 10 wherein the reaction feed includes 1,1,2,2,2-pentachloroethane, and the method further includes reacting 1,1,2,2,2-pentachloroethane with germanium tetrafluoride at a molar ratio of about 1:15:45 for antimony chloride/1,1,2,2,2-pentachloroethane/germanium tetrafluoride.

17. The method of claim 10 wherein the reaction feed includes 1,1,2,2,2-pentachloroethane, and the method further includes reacting 1,1,2,2,2-pentachloroethane with germanium tetrafluoride while germanium tetrafluoride is in molar excess over 1,1,2,2,2-pentachloroethane, and wherein the method further includes scrubbing excess germanium tetrafluoride with a material containing potassium hydroxide and/or sodium hydroxide.

18. The method of claim 10, further comprising producing a reaction product containing hydrohalocarbon compounds consisting essentially of 1,1,2-trichloro-2,2-difluoroethane ($CHCl_2CClF_2$).

19. The method of claim 10, further comprising distilling the produced reaction product containing 1,1,2,2-pentachloro-2-fluoroethane and 1,1,2-trichloro-2,2-difluoroethane and separating 1,1,2,2-pentachloro-2-fluoroethane from 1,1,2-trichloro-2,2-difluoroethane in the reaction product.

20. A method for producing hydrofluorocarbon compounds, comprising:
loading a charge containing 1,1,2,2,2-pentachloroethane ($Cl_2CHCCl_3$) and antimony pentachloride ($SbCl_5$) into a reactor;
flowing a feed gas containing germanium tetrafluoride ($GeF_4$) into the reactor; and
reacting 1,1,2,2,2-pentachloroethane of the charge with germanium tetrafluoride of the feed gas in the presence of antimony pentachloride in the reactor.

21. The method of claim 20, further comprising discharging a reaction product containing at least one of 1,1,2,2-pentachloro-2-fluoroethane ($CHCl_2CCl_2F$) and 1,1,2-trichloro-2,2-difluoroethane ($CHCl_2CClF_2$) from the reactor.

22. The method of claim 21 wherein the reaction product is at least partially a liquid at a temperature less than about 70° C.

23. The method of claim 20, further comprising heating the reactor to a temperature of about 60° C. to about 90° C. before flowing the feed gas into the reactor.

24. The method of claim 20 wherein reacting 1,1,2,2,2-pentachloroethane of the charge with germanium tetrafluoride of the feed gas includes reacting 1,1,2,2,2-pentachloroethane with germanium tetrafluoride with a conversion greater than about 60%.

25. A method for producing chlorofluorocarbon compounds, comprising:
contacting a first reagent containing 1,1,2,2,2-pentachloroethane ($Cl_2CCCl_3$) with a second reagent containing germanium tetrafluoride ($GeF_4$) in the presence of a catalyst containing antimony pentachloride ($SbCl_5$);
concurrently forming a series of equilibria between species of $SbCl_xF_y$ (x+y=5) and species of $GeCl_aF_b$ (a+b=4);
fluorinating 1,1,2,2,2-pentachloroethane in the first reagent with germanium tetrafluoride in the second reagent while catalyzed by the species of $SbCl_xF_y$ (x+y=5).

26. The method of claim 25 wherein fluorinating 1,1,2,2,2-pentachloroethane includes shifting the series of equilibria to produce a product from the reaction with a selectivity toward 1,1,2,2-pentachloro-2-fluoroethane ($CHCl_2CCl_2F$) and 1,1,2-trichloro-2,2-difluoroethane ($CHCl_2CClF_2$)

* * * * *